(12) United States Patent
Glendening et al.

(10) Patent No.: US 6,245,552 B1
(45) Date of Patent: Jun. 12, 2001

(54) METHOD FOR WASTE DEGRADATION

(75) Inventors: Larrick H. Glendening, Bradenton; Vincent J. Scuilla, Sarasota, both of FL (US)

(73) Assignee: Osprey Biotechnics, Inc., Sarasota, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/376,299

(22) Filed: Jan. 23, 1995

Related U.S. Application Data

(63) Continuation of application No. 08/186,170, filed on Jan. 25, 1994, now abandoned, which is a continuation-in-part of application No. 07/834,771, filed on Feb. 13, 1992, now Pat. No. 5,935,843.

(51) Int. Cl.$^7$ ................................ C12S 9/00; C12S 13/00
(52) U.S. Cl. .......................... 435/262; 435/264; 210/606
(58) Field of Search ................ 435/34, 243, 252.34, 435/252.5, 253.6, 260, 262, 262.5, 281, 810; 210/605, 610, 611

(56) References Cited

U.S. PATENT DOCUMENTS

| | | | |
|---|---|---|---|
| 4,138,036 | * 2/1979 | Bond | 222/105 |
| 4,385,121 | * 5/1983 | Knowlton | 435/244 |
| 4,415,085 | * 11/1983 | Clarke et al. | 206/526 |
| 4,452,894 | 6/1984 | Olsen et al. | 435/253 |
| 4,593,003 | 6/1986 | Vandenbergh | 435/172.3 |
| 4,672,037 | * 6/1987 | Daggett et al. | 435/253 |
| 4,673,505 | 6/1987 | Wong | 210/611 |
| 4,786,192 | * 11/1988 | Graves et al. | 383/119 |
| 4,822,490 | 4/1989 | Dyadechko et al. | 210/611 |
| 4,910,143 | 3/1990 | Vandenbergh | 435/252.34 |
| 4,911,832 | * 3/1990 | Miller et al. | 210/86 |
| 4,956,295 | 9/1990 | Sudoma | 435/232.1 |
| 4,970,000 | 11/1990 | Eppler et al. | 210/605 |
| 4,994,391 | * 2/1991 | Hoffman | 435/286 |
| 4,999,301 | 3/1991 | Bryan-Jones | 435/252.5 |
| 5,039,415 | 8/1991 | Smith | 210/610 |
| 5,185,080 | 2/1993 | Boyle | 210/611 |

FOREIGN PATENT DOCUMENTS

| | | | |
|---|---|---|---|
| 9002167 | * 3/1990 | (WO) | 435/287 |

OTHER PUBLICATIONS

Vandenbergh, P.A. and A.M. Wright, Appl. Environ. Microbiol. 45:1953–1955 (1983).
Vandenbergh, P.A., C.F. Gonzalez, A.M. Wright ) and B. S. Kunka, Appl. Environ. Microbiol. ) 46:128–132 (1983).
Vandenbergh, P.A., R.H. Olsen and J.F. Colaruotolo, Appl.Environ. Microbiol. 42:737–739 (1981).
Vandenbergh, P.A. and R.L. Cole, Appl. Environ. Microbiol. 52:939–940 (1986).

\* cited by examiner

*Primary Examiner*—William H. Beisner
(74) *Attorney, Agent, or Firm*—Ian C. McLeod

(57) ABSTRACT

A method for growing waste degrading microorganisms on site and then adding them to the waste is described. The microorganisms are initially cultivated and concentrated to between about $10^{11}$ and $10^{13}$ cells per gram, dried and then placed in bags (11) or other collapsible containers with a dried, growth medium at $10^{10}$ or more cells per container for shipment to end users. To activate the microorganisms, the bags or other container containing the microorganisms and the medium are filled with water. The microorganisms are allowed to grow for at least about 24 and not more than about 32 hours and at that time the number of bacteria will have increased by one log. The microorganisms and medium are then added to the waste material so that the microorganisms can feed on and degrade the waste.

14 Claims, 3 Drawing Sheets

METHOD FOR WASTE DEGRADATION

CROSS-REFERENCE TO RELATED APPLICATION

This is a continuation of application Ser. No. 08/186,170 filed on Jan. 25, 1994, now abandoned. Which is a continuation-in-part of application Ser. No. 07/834,771, filed Feb. 13, 1992 now U.S. Pat. No. 5,935,843.

BACKGROUND OF THE INVENTION (1) Field of the Invention

The present invention relates to a method for providing microorganisms in an organic waste system for degrading organic wastes into carbon dioxide and water. In particular, the present invention relates to a method wherein the microorganisms are grown on site in a container for up to about 32 hours prior to addition to the waste system. The microorganisms after being grown on site on the growth medium to a level of at least about $10^9$ cells/ml can be added to the organic wastes to degrade them at a sufficient dosage, usually at about $10^6$ cells/ml of organic waste.

(2) Prior Art

Organic compounds have been shown to be degraded as described in the following references: U.S. Pat. No. 4,452,894 to Olsen et al; U.S. Pat. No. 4,593,003 to Vandenbergh; Vandenbergh, P. A. and A. M. Wright, Appl. Environ. Microbiol. 45:1953–1955 (1983); Vandenbergh, P. A., C. F. Gonzalez, A. M. Wright and B. S. Kunka, Appl. Environ. Microbiol. 46:128–132 (1983); Vandenbergh, P. A., R. H. Olsen and J. F. Colaruotolo, Appl. Environ. Microbiol. 42:737–739 (1981); and Vandenbergh, P. A., and R. L. Cole, Appl. Environ. Microbiol. 52:939–940 (1986). The useful application of bacteria to the environment to degrade organic wastes has been previously demonstrated by U.S. Pat. No. 4,593,003 to Vandenbergh. Also, U.S. Pat. No. 4,910,143 to Vandenbergh describes a mixture of *Pseudomonas putida* strains for degrading an organic waste of the kind that are commonly found in the environment. Also, U.S. Pat. No. 4,673,505 to Wong; 4,822,490 to Dyadechko et al; U.S. Pat. No. 4,956,295 to Sudoma; U.S. Pat. No. 4,970,000 to Eppler et al; U.S. Pat. No. 4,999,301 to Bryan-Jones; U.S. Pat. No. 5,039,415 to Smith; and U.S. Pat. No. 5,185,080 to Boyle show various bacteria and methods for organic waste degradation.

The problem with the prior art methods is that it is too costly for a culture supply house to provide sufficient microbial cells on site for direct inoculation at an effective level into the organic waste compositions. The shipping costs are also significant for such large amounts of culture. The user on the other hand needs as many cells as possible for the degradation of the wastes. There is thus a need for a method which provides this level of microbial cells on site for inoculation into the organic wastes.

OBJECTS

It is therefore an object of the present invention to provide a method for growing specific cells in a disposable, microbiologically prepared (essentially aseptic) container so that the cells multiply by 10 within 24 hours and under acceptable microbial conditions to eliminate the growth of unwanted bacteria cells. It is further an object of the present invention to provide a method which uses multiplied cells for degrading an organic waste, wherein sufficient cells are grown at the site for inoculation of the microorganisms into the waste material, preferably at least about $10^6$ cells/ml of the organic wastes. Further still, it is an object of the present invention to provide a method for degrading organic wastes using microorganisms that is relatively inexpensive and easy to use. These and other objects will become increasingly apparent by reference to the following description and to the drawings.

DESCRIPTION OF PREFERRED EMBODIMENTS

Figure 1:
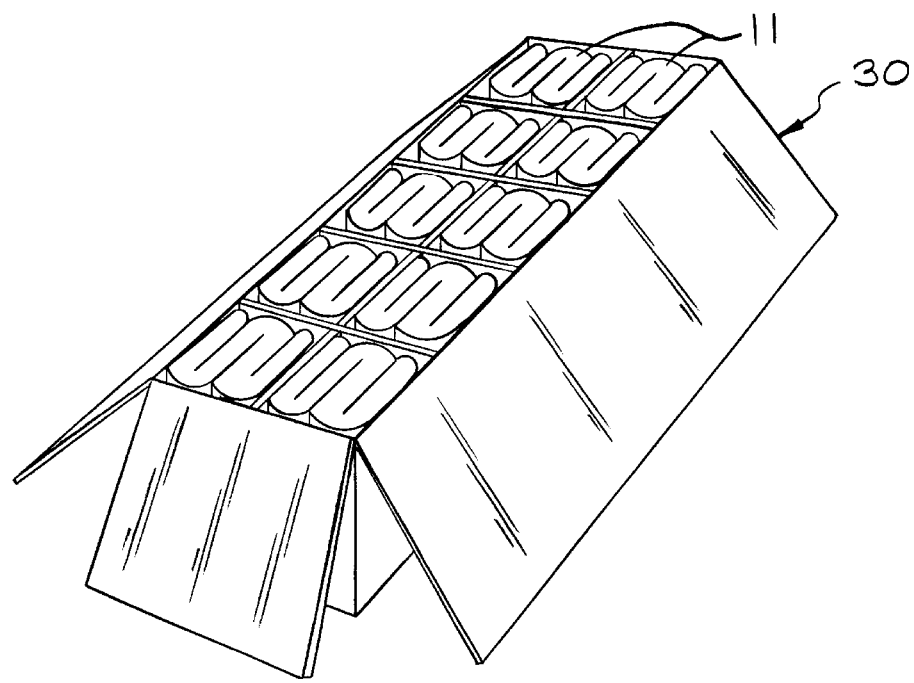
FIG. 1 is a perspective view of a plurality of flexible plastic bags 11 containing the microorganisms 15 for the organic waste degradation packaged in a carton 30 for shipping.
Figure 2:
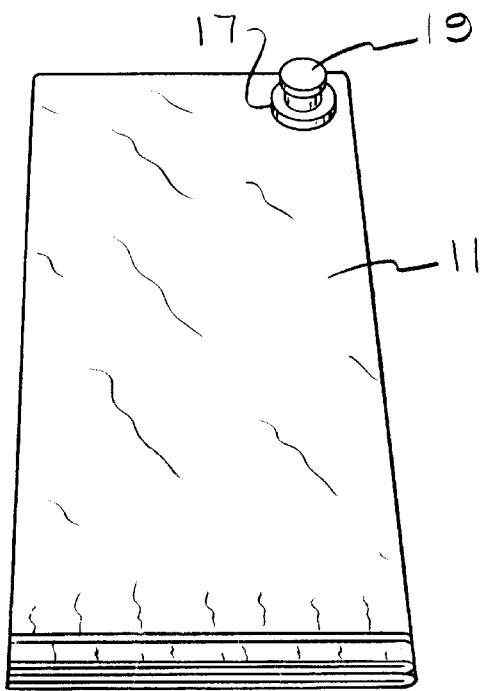
FIG. 2 is a perspective view of a single bag 11 containing the microorganisms 15.

The present invention relates to a method for treating an organic waste material to degrade the waste, which comprises: providing a dried microorganism which can degrade the waste admixed with a dried growth medium for the microorganism in a sealed, disposable, container with a closeable opening into the container wherein the bacteria are present in a number of at least about $1 \times 10^{10}$ CFU for shipment to a user; providing the container near the site where the microorganisms are to be introduced into the waste; filling the container through the opening with water so as to form a liquid growth medium with the microorganism; holding the microorganisms in the liquid culture medium in the container for a period of time of up to about 32 hours and at a temperature so that the microorganisms grow at least ten times the number initially present after filling the bag; and adding the microorganisms along with the liquid growth medium to the waste. The containers are then thrown away or recycled as a waste material, but are not reused.

The present invention also relates to a method for treating an organic waste to degrade the waste, which comprises: providing a dried microorganism which can degrade the waste admixed with a dried growth medium for the microorganism in a sealed disposable bag with a closeable opening into the bag wherein the bacteria are present in a number of at least about $10^{10}$ CFU at a site where the waste is to be degraded; mounting the bag in a containment means near the site where the microorganisms are to be introduced into the waste material so that the bag is supported and can be filled with water; filling the bag through the opening with water so as to form a liquid growth medium with the microorganism; holding the microorganisms in the liquid culture medium in the bag supported by the containment means for a period of time up to about 32 hours (preferably between about 24 and 32 hours) and at a temperature so that the microorganisms grow at least ten times the number initially present after filling the bag; and adding the microorganisms along with the liquid growth medium to the waste. The bag is then thrown away or recycled as a waste material, but is not reused. Preferably the microorganisms are at a level of $10^{12}$ CFU in the bag or other container before the water is added and about $10^8$ per ml of water after the water is added and before the culture is grown in growth medium.

The microorganisms used are preferably Pseudomonas and Bacillus; however, other bacteria and also fungi are also known to degrade waste. Such microorganisms are well known to those skilled in the art as previously discussed. Usually the microorganisms are aerobic; however, they can be anaerobic.

The microorganisms are grown in various growth media prior to shipment to the user. The microorganisms can usually be grown in a growth medium containing yeast extract, dextrose, tryptone, potassium nitrate and sodium chloride. The yeast extract provides nitrogen and vitamins. The inorganic salts aid growth. Normally bacterial strains only grow to about $10^9$ cells per gram and stay at this level without removal of some of the growth medium. The cells are concentrated up to about $10^{11}$ and $10^{13}$ cells per gram. The microbial cells are preferably freeze-dried or lyophilized as is well known to those skilled in the art. Other methods involving air drying the cells is also known and the cells can be held at room temperature.

The dried microorganisms are then admixed with a powdered carbohydrate source for the microorganism such as lactose, dextrose or sucrose; potassium or sodium nitrate; and powdered soy and yeast extract or another nitrogen source in the bag (or other container) so that there are at least $10^{10}$ cells in the container and preferably between $10^{10}$ and $10^{14}$ cells. The nitrate is an important ingredient since it inhibits the growth of unwanted bacteria in the closed bag system. The nitrate is preferably used in amounts between about 15 and 45 percent by weight of the growth medium. The carbohydrate is preferably between about 25 and 40 percent of the growth medium. The nitrogen source is usually about 30 to 50 percent of the growth medium. This insures that the cells will grow when water is added to the mixture, thus enabling the microorganisms to increase when water is added by at least one log (10 times) in 24 to 32 hours without causing the cells to have a reduced capability of degradation of the waste. Contaminant bacteria are inhibited by the nitrate. There are preferably about $10^8$ cells per ml in the container upon addition of the water. The microorganisms are preferably held at reduced temperatures before water is added. The cells are then allowed to grown on site at temperatures at or above ambient household temperatures for 24 to 32 hours until at least about $10^9$ cells per ml are produced in the container. The growth should take place at a temperature of about 59° F. to 95° F. (15° C. to 35° C.) and the filled bag should be moved into a heated enclosure, if required, to meet this temperature. The cells are then added to the waste. Generally the site is an industrial lagoon, tank or soil containing waste materials to be degraded. The bag is then thrown away or recycled as waste, but not reused.

EXAMPLE 1

Figure 3:
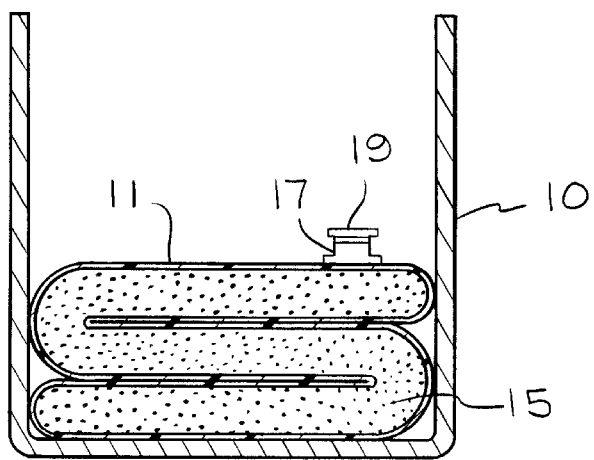
FIG. 3 is a front cross-sectional view showing the collapsed bag 11 in a container 10.
Figure 4:
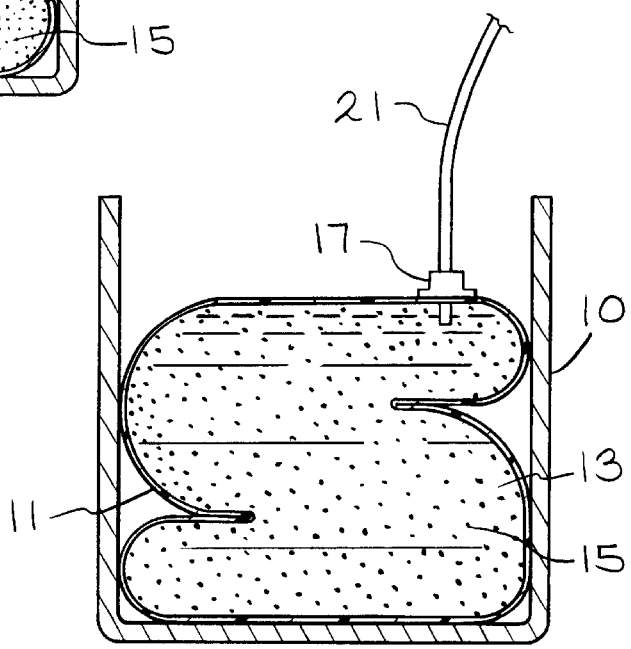
FIG. 4 is a front cross-sectional view of a container 10 with a partially filled bag 11 supplied by hose 21.
Figure 5:
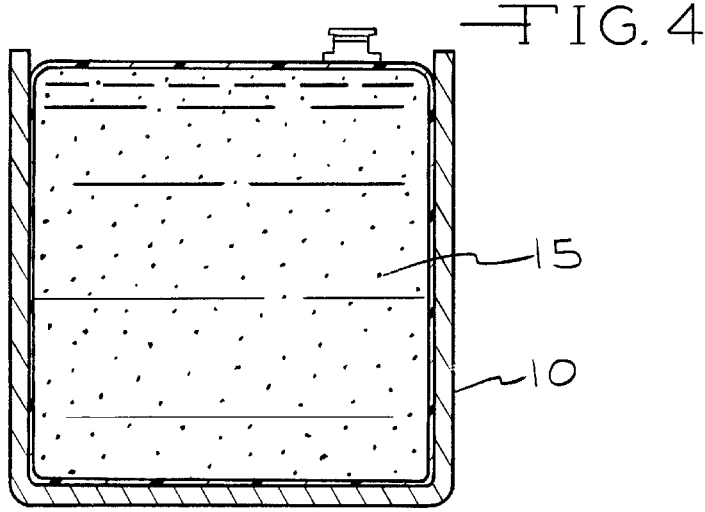
FIG. 5 is a front cross-sectional view of the filled bag 11 in the container 10.

FIGS. 1 to 6 illustrate the preferred method for growing and using the microorganisms to degrade the wastes. A carton 30 is used to ship bags 11 containing the dried microorganisms 15 (FIGS. 3 to 5). The containment unit 10 supports a bag 11 for holding an aqueous solution 13 of microorganisms 15. A solution feed hose 21 is used to introduce water into the bag 11 through a filler opening 17 prior to allowing the microorganisms to grow on site.

In the manufacture of a concentrate of the bacteria, the microorganisms 15 were grown in a growth medium as explained above to a level of about $10^6$ cells per ml. The microorganisms 15 were then preferably freeze-dried or lyophilized and held at reduced temperatures, preferably between about −20° F. and −4° F. (−29° C. and −20° C.) to preserve the viability of the microorganisms 15 prior to use.

The process of drying, such as by freeze-drying or lyophilizing the microorganisms 15, can be extremely damaging to the microorganisms 15. Typically, between 60% to 70% of the microorganisms 15 perish during the lyophilizing process. However, the concentration of microorganisms 15 is large enough before the lyophilizing process that a significant number survive the lyophilizing process. The concentration of microorganisms 15 that survive the lyophilizing or freeze-drying process was between about $10^{10}$ and $10^{14}$ cells per gram. The microorganisms 15 can also be preserved by air drying. The air drying process takes place at elevated temperatures which maintain the viability of the microorganisms 15. The air drying process is known to those skilled in the art and produces large losses of viability of the microorganisms.

After the microorganisms 15 have been concentrated and dried, the microorganisms 15 were placed in the bags 11 along with the growth medium for shipment. The microorganisms were mixed with a dry powdered medium including soy digest 23.57 grams (9%), yeast extract 95 grams (36%), sodium nitrate 49.4 grams (19%) and dextrose 95 grams (36%). The soy digest and yeast extract are nitrogen sources, the nitrate is an oxygen source and preservative and the dextrose is a carbon source. A substantial amount of the alkali metal nitrate is important so that the anaerobic bacteria can grow in the bag and any contaminant bacteria are suppressed. It prevents the growth of contaminant microorganisms for up to 32 hours.

As shown in FIG. 1, the bags 11 were folded to minimize space and packaged in a shipping carton 30. There were preferably ten (10) bags 11 per carton 30. It is preferred that the carton 30 containing the bags 11 be stored in a freezer before use to maintain the dried microorganisms 15 in a viable state. Refrigerating the carton 30 can be done by any acceptable means. Preferably, the carton 30 is packed in dry ice or is shipped in a refrigerated shipping container (not shown). Microorganisms 15 which were preserved by air drying could be held at room temperatures.

The microorganisms 15 can be light sensitive and thus die faster when exposed to light. Therefore, the bags 11 are preferably made of a flexible, plastic material such as polypropylene, which is opaque or translucent to reduce the amount of light reaching the microorganisms 15.

To prepare the microorganisms 15 for use on site, a bag 11 containing the microorganisms 15 was first placed in the containment unit 10, as shown in FIGS. 3 to 5. The containment unit 10 preferably has a circular, cross-section. A filler opening 17 and cover 19 is provided in the top of the bag 11. The filler opening 17 is preferably made of an elastic material.

As shown in FIGS. 4 and 5, the aqueous solution 13 of the microorganisms 15 was made on site by adding water to the bag 11. A filler hose 21 was inserted into the filler opening 17 to fill the bag 11 with warm water until the bag 11 expands to the confines of the inside of the unit 10. The water brings the microorganisms 15 to temperatures at or above ambient household temperatures, and activates the microorganisms 15 from their lyophilized or air-dried state. The water was preferably held at a temperature of between about 59° F. and 95° F. (15° C. and 35° C.). The bag 11 held in the unit 10 is preferably capable of holding about 5 to 55 gallons (18.9 liters) of the aqueous solution 13 of microorganisms 15.

Figure 6:
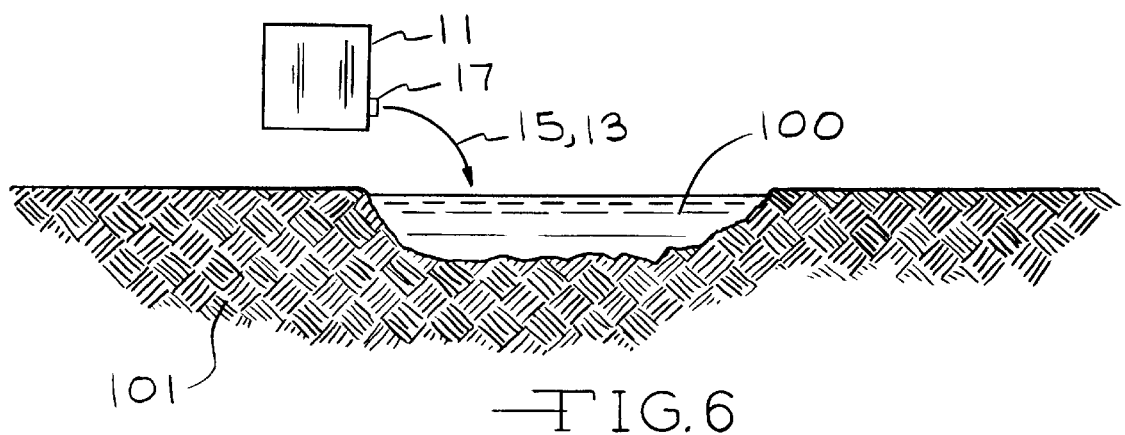
FIG. 6 is a perspective view of a pond 100 surrounded by land with the contents of the bag 11 being introduced into pond 100.
Figure 7:
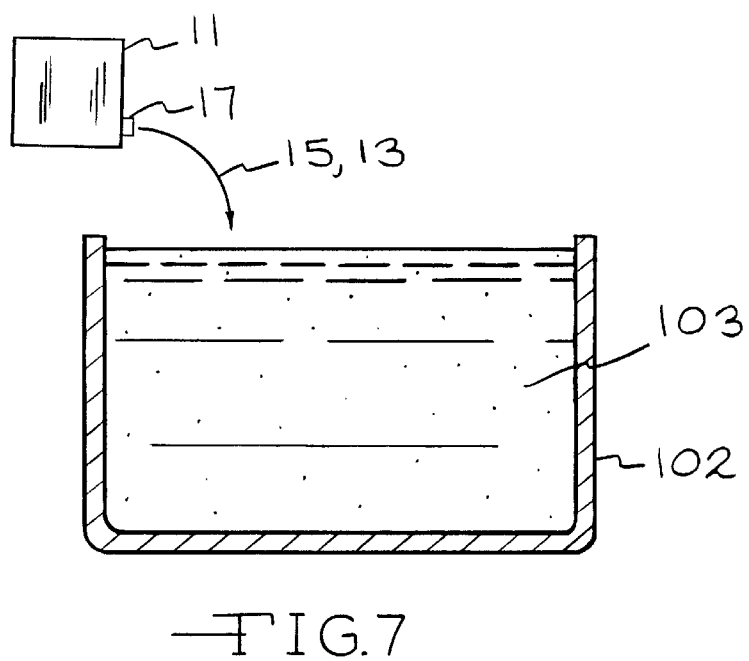
FIG. 7 is a front cross-sectional view of a tank 102 filled with a waste material to be degraded to which the microorganisms 15 are being added.
Figure 8:
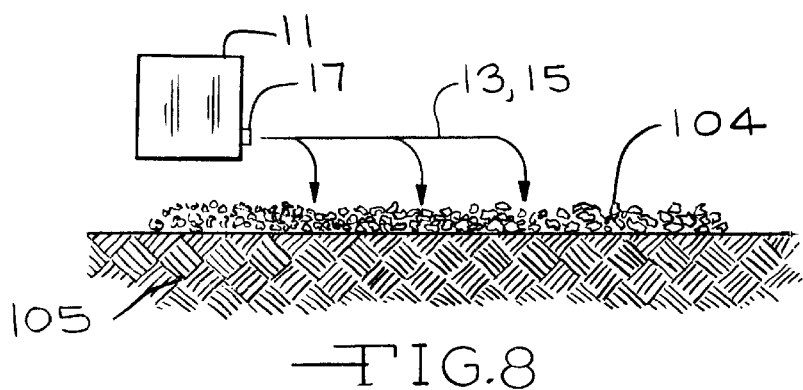
FIG. 8 is a front cross-sectional view of loose soil 104 on land 105 to which the microorganisms 15 are being added.

Once the bag 11 was filled, the microorganisms were allowed to grow one log (10 times) from $10^8$ to $10^9$ cells per ml in about 24 to 32 hours. The method was particularly used to degrade phenol in a pond 100 surrounded by soil 101 as shown in FIG. 6; in a tank 102 containing waste 103 as shown in FIG. 7; or in loose soil 104 on land 105 as shown in FIG. 8.

It is intended that the foregoing description be only illustrative of the present invention and that the present invention be limited only by the hereinafter appended claims.

What is claimed is:

1. A method for treating an organic industrial waste to degrade the waste, which comprises:
   (a) providing dried cells of a microorganism which is anaerobic and can degrade the waste admixed with a dried growth medium for the microorganism containing an alkali metal nitrate in an amount between about 15 and 45 percent by weight of the growth medium in a sealed container with folds which collapses the container for shipment of multiple containers in a single box and with a closeable opening on the container, wherein the folds are horizontally opposite each other;
   (b) shipping the collapsed container near a site where the microorganism is to be introduced into the waste;
   (c) providing the collapsed container in a containment means so that the folds are below the closeable opening and the folds engage the containment means as the container is filled;
   (d) filling the container through the opening with water so as to unfold the container and to form a liquid growth medium from the dried growth medium admixed with the microorganism;
   (e) holding the microorganism in the liquid growth medium in the container for a period of time of up to about 32 hours and at a temperature so that the microorganisms grow and increase in cell number and wherein the alkali metal nitrate and the microorganism inhibit any contaminant microorganisms in the liquid growth medium; and
   (f) adding the microorganism along with the liquid growth medium to the industrial waste in a treatment plant, a lagoon, a tank or a soil, wherein the waste is degraded.

2. The method of claim 1 wherein the microorganism is naturally occurring soil microorganism selected from the group consisting of Pseudomonas and Bacillus.

3. The method of claim 1 wherein the microorganism is a naturally occurring soil Pseudomonas.

4. The method of claim 1 wherein in step (e) the microorganism is held in the container for between about 24 and 32 hours.

5. The method of claim 1 wherein the growth medium contains sodium nitrate as the alkali metal nitrate.

6. The method of claim 1 wherein the site is an outdoor waste pond into which the microorganism in step (f) is added.

7. The method of claim 1 wherein the site is a soil into which the microorganism in step (f) is added.

8. The method of claim 1 wherein the site is a tank containing the waste.

9. The method of claim 1 wherein the site is a waste treatment plant.

10. A method for treating an organic industrial waste to degrade the waste, which comprises:
    (a) providing dried cells of a microorganism which is anaerobic and can degrade the waste admixed with a dried growth medium for the microorganism containing an alkali metal nitrate in an amount between about 15 and 45 percent by weight of the growth medium in a sealed flexible bag with folds for shipment of multiple containers in a single box to a site where the waste is to be degraded and with a closeable opening on the bag, wherein the folds are horizontally and alternately opposite each other wherein the microorganism is present in a number of at least about $10^{10}$ CFU;
    (b) shipping the collapsed bag to a site where the microorganism is to be introduced into the waste;
    (c) mounting the bag in a containment means near the site where the microorganism is to be introduced into the waste so that the bag is supported and can be filled with water;
    (d) filling the bag through the opening with water so as to unfold the bag and form a liquid growth medium with the microorganism, wherein the folds are below the closeable opening and engage the containment means as the bag is filled;
    (e) holding the microorganism in the liquid growth medium in the bag supported by the containment means for a period of time up to about 32 hours and at a temperature so that the microorganism grows and increases in cell number to at least about $10^9$ cells per ml and wherein the alkali metal nitrate and the microorganism inhibit any contaminant microorganisms; and
    (f) adding the microorganism along with the liquid growth medium to the industrial waste in a treatment plant, a lagoon, a tank or a soil, wherein the waste is degraded.

11. The method of claim 10 wherein the containment means is a crate and after the bag is unfolded and filled with water to form the liquid growth medium, the bag holds about 5 gallons of the liquid growth medium in the crate.

12. The method of claim 10 wherein the containment means is a drum and after the bag is unfolded and filled with water to form the liquid growth medium, the bag holds about 55 gallons of the liquid growth medium in the drum.

13. The method of claim 10 wherein the bag is made of blow molded polypropylene.

14. The method of claim 10 wherein the growth medium contains sodium nitrate as the alkali metal nitrate.

* * * * *